(12) United States Patent
Glossop

(10) Patent No.: US 7,751,868 B2
(45) Date of Patent: Jul. 6, 2010

(54) INTEGRATED SKIN-MOUNTED MULTIFUNCTION DEVICE FOR USE IN IMAGE-GUIDED SURGERY

(75) Inventor: Neil David Glossop, Toronto (CA)

(73) Assignee: Philips Electronics Ltd, Vancouver, British Columbia (CA)

( * ) Notice: Subject to any disclaimer, the term of this patent is extended or adjusted under 35 U.S.C. 154(b) by 260 days.

(21) Appl. No.: 11/271,899

(22) Filed: Nov. 14, 2005

(65) Prior Publication Data

US 2006/0173269 A1 Aug. 3, 2006

Related U.S. Application Data

(60) Provisional application No. 60/626,946, filed on Nov. 12, 2004.

(51) Int. Cl.
*A61B 5/05* (2006.01)
*A61B 6/00* (2006.01)

(52) U.S. Cl. ............... 600/426; 600/407; 600/413; 600/422

(58) Field of Classification Search .......... 600/410, 600/415, 426, 421, 414, 407, 424, 431, 413, 600/422; 378/205
See application file for complete search history.

(56) References Cited

U.S. PATENT DOCUMENTS

| | | | |
|---|---|---|---|
| 3,021,842 A | 2/1962 | Flood | |
| 4,080,706 A | 3/1978 | Heilman et al. | ............... 29/173 |
| 4,279,252 A | 7/1981 | Martin | |
| 4,697,595 A | 10/1987 | Breyer et al. | |
| 4,722,056 A | 1/1988 | Roberts et al. | ............... 364/413 |
| 4,777,951 A | 10/1988 | Cribier et al. | |
| 4,887,606 A | 12/1989 | Yock et al. | |
| 4,895,168 A | 1/1990 | Machek | |
| 4,935,019 A | 6/1990 | Papp, Jr. | ............... 604/362 |
| 4,961,433 A | 10/1990 | Christian | |
| 5,014,708 A | 5/1991 | Hayashi et al. | ............... 128/653 R |
| 5,042,486 A | 8/1991 | Pfeiler et al. | |
| 5,045,080 A | 9/1991 | Dyer et al. | ............... 604/362 |
| 5,085,659 A | 2/1992 | Rydell | ............... 606/47 |
| 5,116,345 A | 5/1992 | Jewell et al. | ............... 606/130 |

(Continued)

FOREIGN PATENT DOCUMENTS

AU 6367896 2/1997

(Continued)

OTHER PUBLICATIONS

Tanase, Dafina, et al., "Magnetic Sensors for Use on Guide Wires or Catheters", in *SeSens* 2001, in press 2002, pp. 868-872.

(Continued)

*Primary Examiner*—Eric F Winakur
*Assistant Examiner*—Katherine L Fernandez

(57) ABSTRACT

The invention comprises an integrated skin-mountable multifunction device for use with a computer assisted or image guided surgical system and methods of using the same, wherein the multifunction device includes a patient mountable portion that has at least one position indicating element and at least one imageable pattern whose geometry is known in a coordinate system of the at least one position indicating element, wherein the imageable pattern is visible on an imaging modality. The multifunction device may also include a monitoring device capable of measuring a physiological parameter of a patient for use in gating image or position signals or for other purposes.

23 Claims, 9 Drawing Sheets

U.S. PATENT DOCUMENTS

| | | | |
|---|---|---|---|
| 5,187,658 A | 2/1993 | Cline et al. | |
| 5,204,625 A | 4/1993 | Cline et al. | 324/306 |
| 5,207,675 A | 5/1993 | Canady | 606/40 |
| 5,211,165 A | 5/1993 | Dumoulin et al. | |
| 5,221,283 A | 6/1993 | Chang | 606/130 |
| 5,247,935 A | 9/1993 | Cline et al. | |
| 5,251,127 A | 10/1993 | Raab | |
| 5,251,635 A | 10/1993 | Dumoulin et al. | |
| 5,255,680 A | 10/1993 | Darrow et al. | |
| 5,265,610 A | 11/1993 | Darrow et al. | |
| 5,271,400 A | 12/1993 | Dumoulin et al. | |
| 5,275,165 A | 1/1994 | Ettinger et al. | |
| 5,290,266 A | 3/1994 | Rohling et al. | 604/272 |
| 5,291,010 A | 3/1994 | Tsuji | 250/208.1 |
| 5,291,890 A | 3/1994 | Cline et al. | |
| 5,304,933 A | 4/1994 | Vavrek et al. | 324/318 |
| 5,305,203 A | 4/1994 | Raab | |
| 5,307,812 A | 5/1994 | Hardy et al. | |
| 5,318,025 A | 6/1994 | Dumoulin et al. | |
| 5,323,779 A | 6/1994 | Hardy et al. | |
| 5,327,884 A | 7/1994 | Hardy et al. | |
| 5,353,808 A | 10/1994 | Viera | |
| 5,365,927 A | 11/1994 | Roemer et al. | |
| 5,368,031 A | 11/1994 | Cline et al. | |
| 5,368,032 A | 11/1994 | Cline et al. | |
| 5,377,678 A | 1/1995 | Dumoulin et al. | |
| 5,383,454 A | 1/1995 | Bucholz | |
| 5,383,465 A | 1/1995 | Lesny et al. | |
| 5,386,828 A | 2/1995 | Owens et al. | |
| 5,389,101 A | 2/1995 | Heilbrun et al. | 606/130 |
| 5,391,199 A | 2/1995 | Ben-Haim | 607/122 |
| 5,396,905 A | 3/1995 | Newman et al. | |
| 5,400,383 A | 3/1995 | Yassa et al. | 378/98.2 |
| 5,437,277 A | 8/1995 | Dumoulin et al. | |
| 5,443,066 A | 8/1995 | Dumoulin et al. | |
| 5,443,068 A | 8/1995 | Cline et al. | |
| 5,445,150 A | 8/1995 | Dumoulin et al. | |
| 5,465,732 A | 11/1995 | Abele | |
| 5,480,382 A | 1/1996 | Hammerslag et al. | 604/95 |
| 5,490,840 A | 2/1996 | Uzgiris et al. | 604/22 |
| 5,493,598 A | 2/1996 | Yassa et al. | 378/98.2 |
| 5,526,812 A | 6/1996 | Dumoulin et al. | |
| 5,526,814 A | 6/1996 | Cline et al. | |
| 5,558,091 A | 9/1996 | Acker et al. | |
| 5,603,318 A | 2/1997 | Heilbrun et al. | |
| 5,645,065 A | 7/1997 | Shapiro et al. | |
| 5,646,524 A | 7/1997 | Gilboa | 324/207.17 |
| 5,646,525 A | 7/1997 | Gilboa | 324/207.17 |
| 5,647,373 A | 7/1997 | Paltieli | 128/749 |
| 5,705,014 A | 1/1998 | Schenck et al. | 156/272.4 |
| 5,713,858 A | 2/1998 | Heruth et al. | 604/93 |
| 5,715,166 A | 2/1998 | Besl et al. | |
| 5,715,822 A | 2/1998 | Watkins et al. | |
| 5,740,802 A | 4/1998 | Nafis et al. | |
| 5,749,835 A | 5/1998 | Glantz | 600/424 |
| 5,769,790 A | 6/1998 | Watkins et al. | 600/439 |
| 5,769,861 A | 6/1998 | Vilsmeier | 606/130 |
| 5,848,969 A | 12/1998 | Panescu et al. | 600/462 |
| 5,857,032 A | 1/1999 | Wang et al. | 382/154 |
| 5,868,673 A | 2/1999 | Vesely | 600/407 |
| 5,873,845 A | 2/1999 | Cline et al. | 601/3 |
| 5,880,976 A | 3/1999 | DiGioia, III et al. | 364/578 |
| 5,931,786 A | 8/1999 | Whitmore, III et al. | 600/459 |
| 5,944,023 A | 8/1999 | Johnson et al. | 128/899 |
| 5,978,696 A | 11/1999 | VomLehn et al. | 600/411 |
| 6,016,439 A | 1/2000 | Acker | 600/411 |
| 6,036,682 A | 3/2000 | Lange et al. | 604/529 |
| 6,073,043 A | 6/2000 | Schneider | 600/424 |
| 6,097,978 A | 8/2000 | Demarais et al. | 600/429 |
| 6,106,476 A | 8/2000 | Corl et al. | 600/486 |
| 6,141,576 A | 10/2000 | Littmann et al. | 600/381 |
| 6,147,480 A | 11/2000 | Osadchy et al. | 324/67 |
| 6,165,184 A | 12/2000 | Verdura et al. | 606/148 |
| 6,188,355 B1 | 2/2001 | Gilboa | 342/448 |
| 6,196,980 B1 | 3/2001 | Akerfeldt et al. | 600/585 |
| 6,203,493 B1 | 3/2001 | Ben-Haim | 600/117 |
| 6,203,543 B1 | 3/2001 | Glossop | 606/60 |
| 6,205,411 B1 | 3/2001 | DiGioia, III et al. | 703/11 |
| 6,210,339 B1 | 4/2001 | Kiepen et al. | 600/486 |
| 6,216,029 B1 | 4/2001 | Paltieli | 600/427 |
| 6,226,543 B1 | 5/2001 | Gilboa et al. | 600/407 |
| 6,233,476 B1 | 5/2001 | Strommer et al. | 600/424 |
| 6,235,038 B1 | 5/2001 | Hunter et al. | 606/130 |
| 6,241,690 B1 | 6/2001 | Burkett et al. | 600/585 |
| 6,266,551 B1 | 7/2001 | Osadchy et al. | 600/424 |
| 6,266,552 B1 | 7/2001 | Slettenmark | 600/424 |
| 6,272,370 B1 | 8/2001 | Gillies et al. | 600/411 |
| 6,272,371 B1 | 8/2001 | Shlomo | 600/424 |
| 6,285,898 B1 | 9/2001 | Ben-Haim | 600/374 |
| 6,285,903 B1 | 9/2001 | Rosenthal et al. | 600/433 |
| 6,288,785 B1 | 9/2001 | Frantz et al. | 356/614 |
| 6,308,089 B1 * | 10/2001 | von der Ruhr et al. | 600/338 |
| 6,314,310 B1 | 11/2001 | Ben-Haim et al. | 600/424 |
| 6,317,621 B1 | 11/2001 | Graumann et al. | 600/424 |
| 6,332,089 B1 | 12/2001 | Acker et al. | 600/424 |
| 6,336,906 B1 | 1/2002 | Hammarstrom et al. | 600/585 |
| 6,338,716 B1 | 1/2002 | Hossack et al. | 600/459 |
| 6,356,783 B1 | 3/2002 | Hubbard, Jr. | 600/546 |
| 6,380,732 B1 | 4/2002 | Gilboa | 324/207.17 |
| 6,381,485 B1 * | 4/2002 | Hunter et al. | 600/407 |
| 6,383,174 B1 | 5/2002 | Eder | 606/1 |
| 6,385,482 B1 | 5/2002 | Boksberger et al. | 600/424 |
| 6,427,079 B1 | 7/2002 | Schneider et al. | 600/424 |
| 6,442,417 B1 | 8/2002 | Shahidi et al. | 600/429 |
| 6,468,265 B1 | 10/2002 | Evans et al. | 606/1 |
| 6,473,635 B1 | 10/2002 | Rasche | 600/428 |
| 6,484,118 B1 | 11/2002 | Govari | 702/150 |
| 6,493,589 B1 | 12/2002 | Medhkour et al. | 607/99 |
| 6,498,944 B1 | 12/2002 | Ben-Haim et al. | 600/407 |
| 6,499,488 B1 | 12/2002 | Hunter et al. | 128/899 |
| 6,500,114 B1 | 12/2002 | Petitto et al. | 600/156 |
| 6,512,958 B1 | 1/2003 | Swoyer et al. | 607/117 |
| 6,529,758 B2 | 3/2003 | Shahidi | 600/407 |
| 6,547,782 B1 | 4/2003 | Taylor | 606/14 |
| 6,558,333 B2 | 5/2003 | Gilboa et al. | 600/466 |
| 6,574,492 B1 | 6/2003 | Ben-Haim et al. | 600/374 |
| 6,574,498 B1 | 6/2003 | Gilboa | 600/424 |
| 6,580,938 B1 | 6/2003 | Acker | 600/424 |
| 6,585,654 B2 | 7/2003 | White et al. | 600/463 |
| 6,588,333 B1 | 7/2003 | Homer et al. | 101/32 |
| 6,591,129 B1 | 7/2003 | Ben-Haim et al. | 600/424 |
| 6,593,127 B1 | 7/2003 | McKinnon | 600/411 |
| 6,593,884 B1 | 7/2003 | Gilboa et al. | 342/448 |
| 6,615,155 B2 | 9/2003 | Gilboa | 702/150 |
| 6,619,838 B2 | 9/2003 | Bencini et al. | 378/190 |
| 6,628,987 B1 | 9/2003 | Hill et al. | 607/9 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |
| 6,719,700 B1 * | 4/2004 | Willis | 600/462 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 | 9/2004 | Taimisto | 600/424 |
| 6,893,429 B2 | 5/2005 | Petersen | 604/537 |
| 6,895,268 B1 | 5/2005 | Rahn et al. | 600/429 |
| 6,916,290 B2 | 7/2005 | Hedengren et al. | 600/549 |
| 7,085,400 B1 | 8/2006 | Holsing et al. | 382/103 |
| 7,386,339 B2 | 6/2008 | Strommer et al. | 600/424 |
| 7,570,791 B2 | 8/2009 | Frank et al. | 382/132 |

| | | | | |
|---|---|---|---|---|
| 2001/0008972 | A1 | 7/2001 | Gielen | 607/45 |
| 2001/0011175 | A1 | 8/2001 | Hunter et al. | 606/130 |
| 2001/0031919 | A1 | 10/2001 | Strommer et al. | 600/424 |
| 2001/0031985 | A1 | 10/2001 | Gilboa et al. | 607/1 |
| 2001/0036245 | A1 | 11/2001 | Kienzle, III et al. | 378/4 |
| 2001/0038354 | A1 | 11/2001 | Gilboa | 342/450 |
| 2001/0039419 | A1 | 11/2001 | Francischelli et al. | 606/42 |
| 2001/0047133 | A1 | 11/2001 | Gilboa et al. | 600/429 |
| 2002/0005719 | A1 | 1/2002 | Gilboa et al. | 324/309 |
| 2002/0038102 | A1 | 3/2002 | McFarlin et al. | 604/30 |
| 2002/0042571 | A1 | 4/2002 | Gilboa et al. | 600/429 |
| 2002/0049375 | A1 | 4/2002 | Strommer et al. | 600/407 |
| 2002/0049451 | A1 | 4/2002 | Parmer et al. | 606/108 |
| 2002/0062203 | A1 | 5/2002 | Gilboa | 702/150 |
| 2002/0074005 | A1 | 6/2002 | Hogg et al. | 128/899 |
| 2002/0087101 | A1 | 7/2002 | Barrick et al. | 600/587 |
| 2002/0115931 | A1* | 8/2002 | Strauss et al. | 600/420 |
| 2002/0143317 | A1 | 10/2002 | Glossop | 604/529 |
| 2002/0156363 | A1* | 10/2002 | Hunter et al. | 600/410 |
| 2002/0156417 | A1 | 10/2002 | Rich et al. | 604/65 |
| 2002/0165448 | A1 | 11/2002 | Ben-Haim et al. | 600/424 |
| 2002/0165468 | A1 | 11/2002 | Tolkowsky et al. | 600/587 |
| 2003/0018251 | A1 | 1/2003 | Solomon | 600/427 |
| 2003/0021455 | A1 | 1/2003 | Dixon et al. | 382/132 |
| 2003/0028233 | A1 | 2/2003 | Vardi et al. | 623/1.11 |
| 2003/0030004 | A1 | 2/2003 | Dixon et al. | 250/370.09 |
| 2003/0074011 | A1 | 4/2003 | Gilboa et al. | 606/130 |
| 2003/0092988 | A1 | 5/2003 | Makin | 600/439 |
| 2003/0114778 | A1 | 6/2003 | Vilsmeier et al. | 600/585 |
| 2003/0114846 | A1 | 6/2003 | Fuimaono et al. | 606/41 |
| 2003/0130576 | A1* | 7/2003 | Seeley et al. | 600/426 |
| 2003/0171680 | A1 | 9/2003 | Paltieli | 600/459 |
| 2003/0171739 | A1 | 9/2003 | Murphy et al. | 606/1 |
| 2003/0208102 | A1 | 11/2003 | Gilboa | 600/41 |
| 2003/0208296 | A1 | 11/2003 | Brisson et al. | 700/117 |
| 2003/0216639 | A1 | 11/2003 | Gilboa et al. | 600/424 |
| 2003/0220557 | A1 | 11/2003 | Cleary et al. | 600/409 |
| 2004/0019274 | A1 | 1/2004 | Galloway, Jr. et al. | 600/425 |
| 2004/0024309 | A1 | 2/2004 | Ferre et al. | 600/424 |
| 2004/0034297 | A1 | 2/2004 | Darrow et al. | 600/407 |
| 2004/0034300 | A1 | 2/2004 | Verard et al. | 600/424 |
| 2004/0036867 | A1 | 2/2004 | Jedamzik et al. | 356/243.1 |
| 2004/0077942 | A1 | 4/2004 | Hall et al. | 600/428 |
| 2004/0078036 | A1 | 4/2004 | Keidar | 606/41 |
| 2004/0097804 | A1 | 5/2004 | Sobe | 600/424 |
| 2004/0097805 | A1 | 5/2004 | Verard et al. | 600/428 |
| 2004/0097806 | A1 | 5/2004 | Hunter et al. | 600/434 |
| 2004/0138548 | A1 | 7/2004 | Strommer et al. | 600/407 |
| 2004/0143188 | A1 | 7/2004 | Barzell et al. | 600/439 |
| 2004/0147837 | A1 | 7/2004 | Macaulay et al. | 600/424 |
| 2004/0147939 | A1 | 7/2004 | Rabkin et al. | 606/108 |
| 2004/0158146 | A1 | 8/2004 | Mate et al. | 800/427 |
| 2004/0221853 | A1 | 11/2004 | Miller | 128/207.14 |
| 2004/0234933 | A1 | 11/2004 | Dawson et al. | 434/262 |
| 2004/0249267 | A1 | 12/2004 | Gilboa | 600/424 |
| 2004/0254458 | A1 | 12/2004 | Govari | 600/437 |
| 2005/0033149 | A1 | 2/2005 | Strommer et al. | 600/407 |
| 2005/0038337 | A1 | 2/2005 | Edwards | 600/424 |
| 2005/0049520 | A1 | 3/2005 | Nakao | 600/562 |
| 2005/0054900 | A1 | 3/2005 | Mawn et al. | 600/156 |
| 2005/0059886 | A1 | 3/2005 | Webber | 600/426 |
| 2005/0085715 | A1 | 4/2005 | Dukesherer et al. | 600/424 |
| 2005/0085720 | A1* | 4/2005 | Jascob et al. | 600/424 |
| 2005/0085793 | A1 | 4/2005 | Glossop | 604/529 |
| 2005/0107688 | A1 | 5/2005 | Strommer | 600/424 |
| 2005/0182295 | A1 | 8/2005 | Soper et al. | 600/117 |
| 2005/0182319 | A1 | 8/2005 | Glossop | 600/424 |
| 2005/0228270 | A1* | 10/2005 | Lloyd et al. | 600/424 |
| 2006/0147100 | A1 | 7/2006 | Fitzpatrick | 382/131 |
| 2007/0032862 | A1 | 2/2007 | Weber et al. | 623/1.34 |

FOREIGN PATENT DOCUMENTS

| | | |
|---|---|---|
| AU | 722539 | 8/2000 |
| BR | 9609484 | 12/1999 |
| CA | 2226938 | 2/1997 |
| DE | 69420228 D | 9/1999 |
| DE | 69420228 T | 4/2000 |
| DE | 19845267 C1 | 5/2000 |
| EP | 0 845 959 | 6/1998 |
| EP | 0 654 244 | 8/1999 |
| EP | 1 466 552 | 10/2004 |
| IL | 0107523 | 1/2000 |
| IL | 0114610 | 7/2000 |
| JP | 10-277047 | 10/1998 |
| JP | 2000500031 T | 1/2000 |
| JP | 2005152463 | 6/2005 |
| WO | WO 97/03609 | 2/1997 |
| WO | WO 98/56295 | 12/1998 |
| WO | WO 00/22904 | 4/2000 |

OTHER PUBLICATIONS

Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

Solomon, Stephen B., et al., "Real-Time Cardiac Catheter Navigation on Three-Dimensional CT Images", *Journal of Interventional Cardiac Electrophysiology*, vol. 8, 2003, pp. 27-36.

Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.

Baert, Shirley A. M., et al., "Endpoint Localization in Guide Wire Tracking During Endovascular Interventions", *Academic Radiology*, vol. 10, No. 12, Dec. 2003, pp. 1424-1432.

Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.

Baert, Shirley A. M., et al., "Guide-Wire Tracking During Endovascular Interventions", *IEEE Transactions on Medical Imaging*, vol. 22, No. 8, Aug. 2003, pp. 965-972.

Kobashi, Keiji, et al., "A New Biomechanical Model Based Approach on Brain Shift Compensation", *MICCAI 2003*, LNCS 2878, 2003, pp. 59-66.

Timinger, Holger, et al., "Motion Compensation for Interventional Navigation on 3D Static Roadmaps Based on an Affine Model and Gating", *Physics in Medicine and Biology*, vol. 49, 2004, pp. 719-732.

Lorigo, Liana M., et al., "Curves: Curve Evolution for Vessel Segmentation", *Medical Image Analysis*, vol. 5, 2001, pp. 195-206 (pp. 1-14).

Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., p. 277-284.

Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.

"Semi-Automatic Registration for Image Guided Surgery", Traxtal poster presented at CAOS '99 (Computer Assisted Orthopaedic Surgery, 4th International Symposium), MICCAI, Mar. 17-19, 1999, Davos, Switzerland, 1 page.

Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Springer-Verlag Heidelberg, 2003, pp. 215-222.

Livyatan, Harel, "Calibration and Gradient-Based Rigid Registration of Fluoroscopic X-rays to CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.

SuperDimension, Ltd, web page, updated in Sep. 2005, 1 page.

Schweikard, Achim, et al., "Robotic Motion Compensation for Respiratory Movement During Radiosurgery", *Computer Aided Surgery*, vol. 5, 2000, pp. 263-277.

Solomon, Stephen B., et al., "Real-Time Bronchoscope Tip Localization Enables Three-Dimensional CT Image Guidance for Transbronchial Needle Aspiration in Swine", *Chest*, vol. 114, No. 5, Nov. 1998, pp. 1405-1410.

Ellsmere, James, et al., "A Navigation System for Augmenting Laparoscopic Ultrasound", Center for Integration of Medicine and Innovative Technology, Cambridge, Massachusetts, 8 pages.

Hofstetter, R., et al., "Fluoroscopy Based Surgical Navigation—Concept and Clinical Applications", Maurice E. Muller Institute for Biomechanics, University of Bern, Switzerland, 1997, 3 pages.

Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.

Summers, Ronald M., et al., "Colonic Polyps: Complementary Role of Computer-Aided Detection in CT Colonography", *Radiology*, vol. 225, No. 2, Nov. 2002, pp. 391-399.

Hara, A. K., et al., "Reducing Data Size and Radiation Dose for CT Colonography", *AJR*, vol. 168, May 1997, pp. 1181-1184.

Knaan, Dotan, et al., Effective Intensity-Based 2D/3D Rigid Registration Between Fluoroscopic X-Ray and CT, *MICCAI*, vol. 1, 2003, pp. 351-358.

Gee, A. H., et al., "3D Ultrasound Probe Calibration Without a Position Sensor", CUED/F-INFENG/TR 488, University of Cambridge, Department of Engineering, Sep. 2004, 21 pages.

Lindseth, Frank, et al., "Probe Calibration for Freehand 3D Ultrasound Reconstruction and Surgical Navigation", Dec. 2002, 27 pages.

FUCHS, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep. 22-25, 1996).].

Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan 1996.

RITA StarBurst Soft Tissue Access System and RITA StarBurst Hard Tissue Access System, http://www.ritamedical.com, Rita Medical Systems, Inc., copyright 2002, , 8 pages.

Cool-tip RF Tissue Ablation System, Cool-tip RF System, and Cool-tip Electrodes, http://www.valleylab.com/static/cooltip/products.html, Valleylab, copyright 2004, 4 pages.

LeVeen Needle Electrode, Boston Scientific, printed from http://www.bostonscientific.com/med_specialty/deviceDetail.jhtml?task= tskBasicDevice..., printed on Sep. 13, 2004, 1 page.

Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.

* cited by examiner

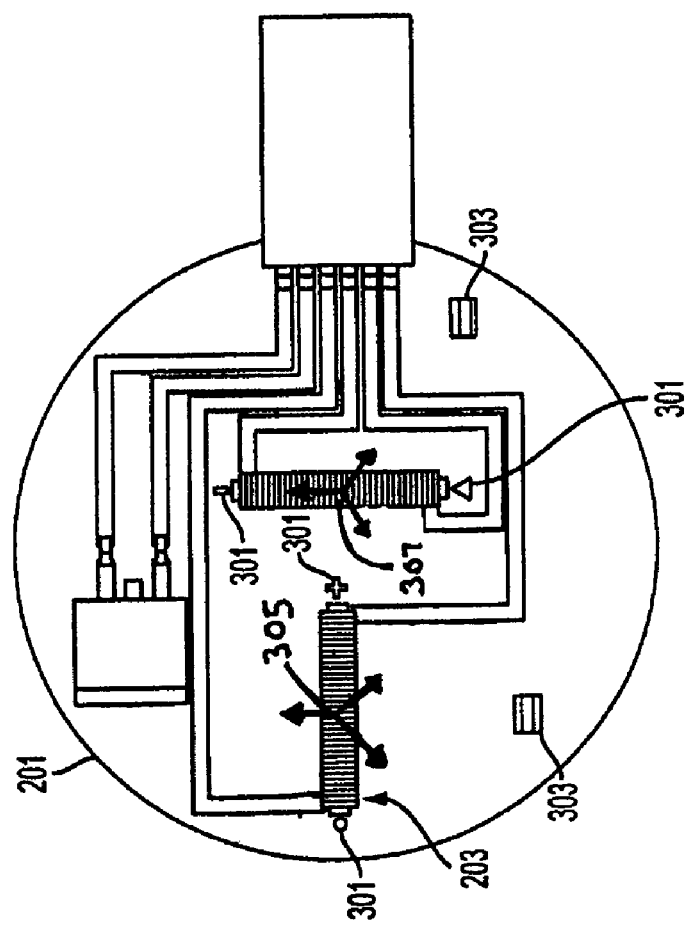
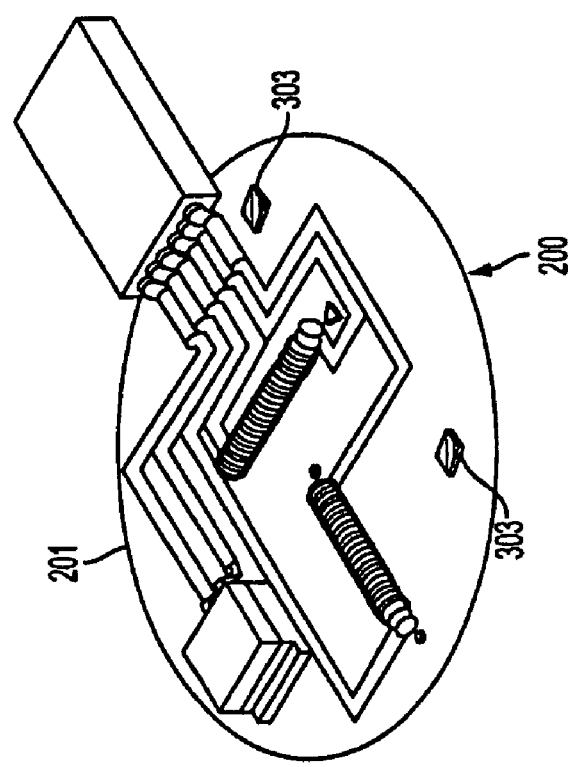
FIG. 3B
FIG. 3A

INTEGRATED SKIN-MOUNTED MULTIFUNCTION DEVICE FOR USE IN IMAGE-GUIDED SURGERY

RELATED APPLICATIONS

This application claims priority to U.S. Provisional Patent Application Ser. No. 60/626,946, filed Nov. 12, 2004, which is hereby incorporated by reference herein in its entirety.

FIELD OF THE INVENTION

This invention relates to an integrated skin mounted multifunction device for use in image guided surgery.

BACKGROUND OF THE INVENTION

Image guided surgery or computer assisted surgery typically utilizes a pre-operative or intraoperative scan or image of a patient to position a device, surgical instrument, or tool during surgery. These images may take various forms and may be acquired using various imaging modalities such as, for example, computerized tomography (CT), magnetic resonance (MR), positron emission tomography (PET), fluoroscopy, x-ray, or other imaging modality. These images are usually taken and transferred to a computer system. The surgical patient may then be moved to an operating room, and a tracking device such as, for example, those using a camera, magnetic field generator, or other device may be connected to the computer system with the images loaded onto it. The tracking device may then track position indicating elements attached to the patient's anatomy to determine the location and orientation of the anatomy. In addition, any tools equipped with position indicating elements may also be tracked and their location and orientation displayed superimposed on a computer display of the scan/image(s).

To prepare for image guided surgery, registration may be performed after pre-operative scanning/imaging. Registration may be performed using various methods depending on the surgical environment, surgical application, or other factors.

There are different ways of registering the position of an anatomical object in a patient coordinate system to views of the anatomical object in an image coordinate system, wherein the anatomical object is relevant to an image guided surgical procedure. The patient coordinate system may be referred to as the "patient space," and may be measured by a tracking device. The image coordinate system may be referred to herein as the "image space," and may be provided by an imaging modality.

A first registration procedure may include "point registration." With point registration, a physician selects landmarks or particular points identified in the pre-acquired images and touches corresponding landmarks or points in the patient's anatomy with a pointer probe having a position indicating element that is tracked by a tracking device. By selecting internal or external anatomical "landmarks" that are identifiable in the pre-acquired images, it is possible to establish a relationship between the two coordinate systems (e.g., the image space of the pre-acquired image, and the patient space of the tracking system). This enables accurate navigation. Often, skin marks are used for this purpose, applied as discrete markers such as ball bearings stuck to the skin.

Another type of registration is a "surface registration" technique. This technique is similar to point registration, except that a tracked pointer probe is dragged or passed along the patient's anatomy, either internally or externally. By using surface recognition software, as is known in the art, the sampled surface can be automatically matched with the corresponding surface in a pre-acquired image. Surface registration may be combined with point registration, as a follow-on step to increase accuracy.

Another technique for registering two different modalities is by a "path registration" technique. The three dimensional path of a natural or artificial conduit in an organ or region of a patient is obtained in a pre-operative scan using an imaging device. A position indicating element is then dragged through the pathway and its coordinates sampled in the patient space by a tracking device. It is then possible to register the shape of the path from the pre-operative image (image space) to the measured path of the sampled coordinates of the position indicating element (patient space) to get an automatic path registration. This method and apparatus has been disclosed in U.S. patent application Ser. No. 11/059,336 (U.S. Patent Publication No. 20050182319), entitled "Method and Apparatus for Registration, Verification, and Referencing of Internal Organs," which is hereby incorporated by reference herein in its entirety.

Another type of registration is called "intrinsic registration," in which a patient is essentially imaged in the same position as the procedure being performed on him or her. Examples of this type of registration are the so-called "fluoroscopic navigation" techniques.

A further type of registration process involves 2D/3D registration of a fluoroscopic image and a pre-operative scan. This minimally-invasive method merges the 3D pre-operative scan with the 2D image. For example, one way to automatically register a patient's heart with fluoroscopy and CT or other imaging modalities is to use nearby bones as anatomical landmarks, or to place objects or devices (such as skin markers) preoperatively so that they are visible in both the 2D and 3D images.

In an additional form of computer assisted surgery, images are not used and therefore no registration is required. In some situations, these "imageless" techniques may operate by determining the proximity of one tracked instrument relative to another or by using a tracked instrument to digitize a surface or a path.

Having performed the registration, it may be advantageous to track the motion of the registered anatomical object during the surgery, so that registration need be performed only once. This may be known as "dynamic referencing." Tracking the motion of the registered anatomical object may also be advantageous to assist with registration. It would be advantageous to provide this tracking in the same device that is used for registration. Dynamic referencing may also be helpful for imageless techniques as it may compensate for gross patient motion which might be mistaken for other movement such as, for example, movement of one instrument toward another instrument, movement of an instrument toward a surface point, or other type of movement.

A process of "gating" may also be used to assist in imaging, registration, imageless computer assisted surgery, or for other purposes. During gating, a signal from a device capable of measuring physiological functions (such as heartbeat or respiration) may be used to trigger acquisition of an image from a scanner or acquisition of a sample from a position sensor or both (e.g., to selectively "gate" data acquisition according to the physiological function). Gating may be combined with traditional dynamic referencing to generate better anatomical dynamic referencing than simple dynamic referencing or gating alone.

Often, multiple additional devices may be attached to the skin of a patient to dynamically reference, register, gate, monitor, image, etc. This may cause problems, as these different devices compete for space in or on a patient.

Often an initial estimate of registration is useful for use in conjunction with other registration techniques that prove greater accuracy. For example, methods such as surface matching or path registration may make use of a mathematical technique known as "iterative closest points" (ICP). This technique is computationally intensive and converges much more rapidly and accurately when supplied with an initial estimate of registration. Such initial estimates may require a manual point-based registration which can be time consuming.

In some forms of computer assisted surgery, especially image-free techniques, hand-eye coordination is improved when a tracked surgical instrument moves on a computer display in the same direction as the surgeon expects it to move (e.g., on a coordinate system that is not rotated at an arbitrary angle relative to the patient). Often the intrinsic coordinate system of a dynamic reference is used as the coordinate system experienced by the surgeon. If a dynamic reference is placed in an arbitrary arrangement (as it usually is), the instrument "sense" (e.g., coordinate orientation) may be arbitrary, leading to difficulty manipulating the instrument (e.g., unexpected directional movement). Alternatively, arbitrary placement of the dynamic reference may require an additional step of rotating surgical images to compensate for such an arbitrary sense or to indicate to a computer the direction of the patient's head and feet so that the image sense is correctly displayed. Thus, a device that automatically corrects these problems would be desirable.

These and other problems exist.

SUMMARY OF THE INVENTION

The invention addresses these and other problems by providing an integrated skin-mounted multifunction device. In one embodiment, the device may comprise multiple layers that can be combined as needed during assembly and packaged into a multifunction device that is convenient and inexpensive to manufacture. In one embodiment, the multifunction device may be disposable. The multifunction device may take the place of several independent devices currently in use in the field of image guided surgery to register, dynamically reference, verify, gate, assist in imaging the patient, or perform other functions.

In some embodiments, the multifunction device may comprise two or more portions that can be removably connected together. In one embodiment, the multifunction device may comprise a patient mountable portion which is capable of being attached to the patient mated to one or more imageable portions containing fiducial marks or imageable pathways visible via an imaging modality. In some embodiments, the one or more imageable portions are imageable using two or more different-imaging modalities. In some embodiments, one or more "operative portions" (e.g., portions containing position indicating elements) may be removably attached to the patient mountable portion or imageable portion. In some embodiments, the patient mountable portions or operative portions may be connected to a "monitoring portion" such as, for example, an ECG monitor. In some embodiments, the imageable portion may include a grid of radio-opaque and visible markings that can also act as an aid to position a needle or other device.

In one embodiment, the multifunction device may include a circuit board. In some embodiments, the circuit board may include a flexible circuit board that is etched with a pattern of conductors so as to form an electronic circuit for distributing power and signals to and from one or more embedded position indicating elements. The circuit board may be attached to a base layer and a cover layer that form a patient mountable portion. The circuit board, the base layer, and the cover layer may be attached together by way of, for example, suitable adhesive, welding processes, or other attachment methods, so as to render the assembled patient mountable portion impervious to fluids and consistent with a device that can be used in a sterile environment.

In some embodiments, the multifunction device may include fiducial marks. The fiducial marks may include marks made of a material that is imageable by an imaging modality (e.g., a radio-opaque material that is visible on an x-ray). The fiducial marks may be embedded within the multifunctional device such as, for example, attached to the circuit board. The fiducial marks may include different, distinguishable flat patterns (e.g., dash, plus sign, triangle, circle or other shapes) or three-dimensional shapes (e.g., spheres, cubes, pyramids, cylinders, or other three-dimensional shapes). The fiducial marks may be attached to the circuit board, the cover layer, base layer, or other part of the multifunction device, so long as the relative location of the fiducial marks remains fixed relative to the origin of a coordinate system of the multifunction device and the position indicating elements. The fiducial marks may be arranged in an asymmetric manner so that they can be readily identified on planar images by comparing the distance between marks and the angles between lines created by joining two marks to a third apex mark.

In one embodiment, the multifunction device may include one or more "imageable patterns." In some embodiments, the one or more imageable patterns may take the form of imageable pathways or imageable regions. The fiducial marks may also be used in, as, or along with the imageable patterns. Imageable pathways may include conduits that are visible to an imaging modality. The imageable pathways may be made through the use of an imageable material (e.g., radio-opaque material that is visible via an x-ray) placed on the multifunction device. For example, when fluoroscopy is used as an imaging modality, an imageable pathway may take the form of a tube or groove in the multifunction device that has been filled with a barium compound. In some embodiments, the imageable pathways may be multiply curved paths whose geometry is well established at the time of manufacture. These multiply curved paths may define a unique orientation and location of the multifunction device. The imageable regions may include zones of unique geometry that are filled with an appropriate material (e.g., one that renders them visible to an imaging modality). Complex imageable patterns (e.g., imageable pathways and imageable regions) may provide superior registration to fiducial marks alone.

In some embodiments, the multifunction device includes a layer that contains an integrated monitor capable of measuring a physiological parameter such as, for example, heart contractions (an electrocardiograph [ECG] electrode), breathing motion, or other physiological parameter. The integrated monitor may not only be used for gathering data regarding a physiological parameter, but also for gating the acquisition of image data (e.g., computerized tomography data during a CT scan or other data gathered by an imaging modality) or gating the use of the multifunction device as a position indicating element in a tracking device. Information regarding the properties of the integrated monitor may be programmed into a memory device of the multifunction device.

In some embodiments, additional functional and/or passive layers may be integrated into the basic design of the multifunction device described herein by adding additional layers.

The various objects, features, and advantages of the invention will be apparent through the detailed description of the preferred embodiments and the drawings attached hereto. It is also to be understood that the following detailed description is exemplary and not restrictive of the scope of the invention.

BRIEF DESCRIPTION OF THE DRAWINGS

FIG. 3A illustrates a circuit board according to an embodiment of the invention.

FIG. 3B illustrates a circuit board according to an embodiment of the invention.

DETAILED DESCRIPTION OF PREFERRED EMBODIMENTS

Figure 1:
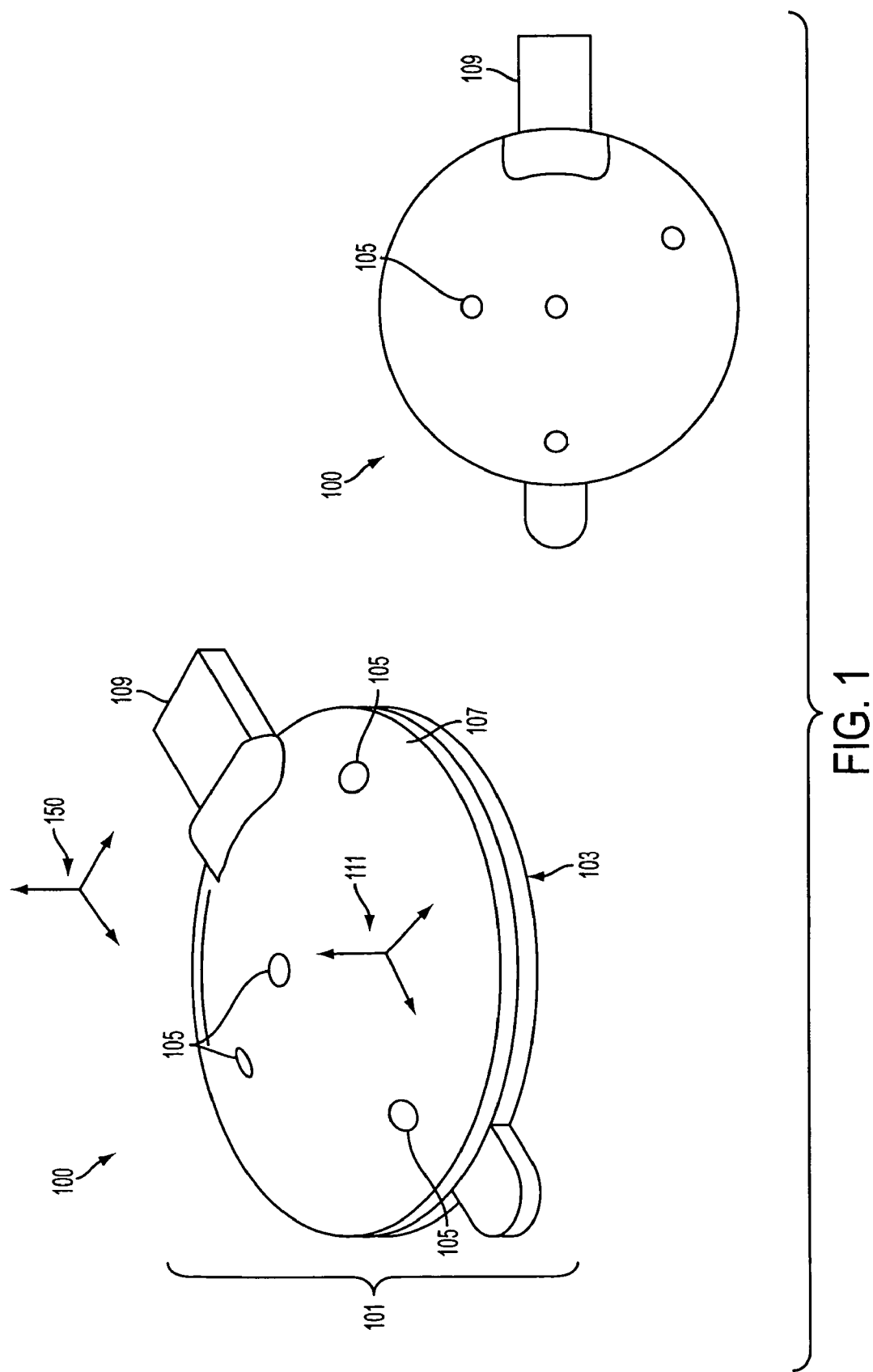
FIG. 1 illustrates a multifunction device according to an embodiment of the invention.

The invention provides an integrated skin-mountable multifunction device for use with an image-guided surgical system and methods for using the device. FIG. 1 illustrates a multifunction device 100 according to an embodiment of the invention. Multifunction device 100 may include a patient mountable portion 101 that may include internal electronics housed within a disposable package. Patient mountable portion 101 of multifunction device 100 may be made of plastic commonly used in medical devices such as, for example, a polycarbonate, ABS, or other material. In some embodiments, the plastic may be radiolucent to assist in visualization of any intrinsic fiducials (discussed below). In some cases, patient mountable portion 101 may be made of a material suitable for fabrication by injection molding.

In some embodiments, the patient mountable portion may have a pressure sensitive adhesive applied to a patient mountable surface 103 (e.g., the "underside" or bottom of the base layer of patient mountable portion 101). In one embodiment, the pressure sensitive adhesive may be capable of securely fastening multifunctional device 100 to a patient's skin surface, thus, enabling multifunction device 100 to act as a "stick on" patch.

In some embodiments, multifunctional device 100 may also include surface features in the form of grooves or divots 105 that may be palpated using a probe or pointer. These surface features may exist on a palpable surface 107 (e.g., the "top" side or cover layer of patient mountable portion 101). In one embodiment, divots 105 may be asymmetrically arranged, so that they are distinguishable from one another.

In some embodiments, multifunctional device 100 may also include an exit point 107 for a cable, wire, or other connector.

In one embodiment, multifunctional device 100 may be associated with an intrinsic coordinate system 111, which defines the location and orientation of multifunctional device 100 and all features contained therein. In some embodiments, the location and orientation of multifunctional device 100 may be determined in terms of the reference frame 150 of a tracking device.

Figure 2:
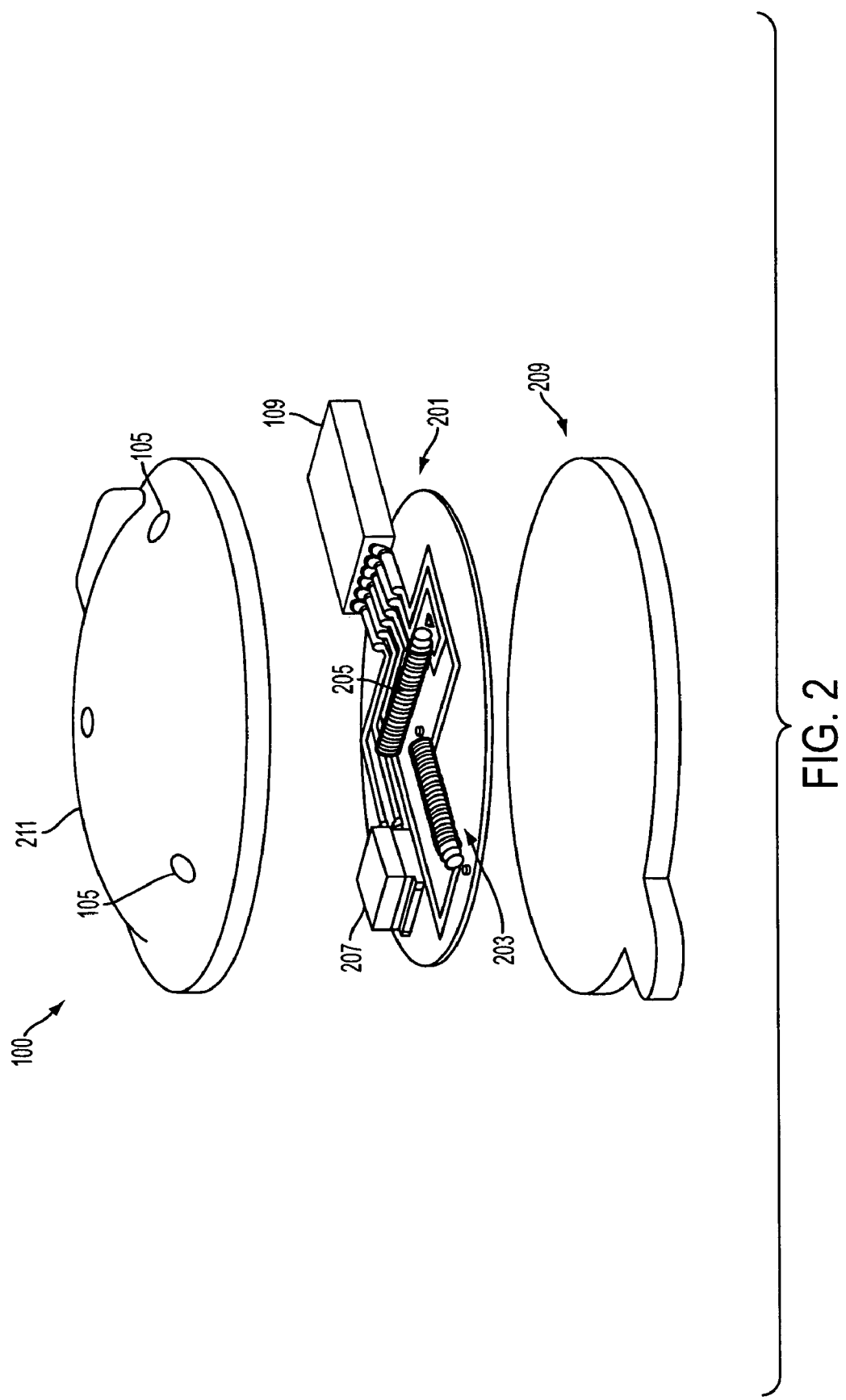
FIG. 2 illustrates a multifunction device according to an embodiment of the invention.

FIG. 2, illustrates an embodiment of the internal construction of multifunction device 100 in detail. In one embodiment, multifunction device 100 may include a circuit board 201. In some embodiments, circuit board 201 may comprise a flexible circuit board that is etched with a pattern of conductors so as to form an electronic circuit for distributing power and signals to one or more embedded position indicating elements 203 and 205. While position indicating elements 203 and 205 are shown here as coils, other types of configurations may be used. Additionally, while position indicating elements 203 and 205 are shown here as discrete components, In some embodiments, they could equally be etched into the circuit board itself.

Circuit board 201 may also include an intrinsic memory device 207 integrated into it. Circuit board 201 may be attached to a base layer 209 and a cover layer 211 that form patient mountable portion 101 (illustrated in FIG. 1). Circuit board 201, base layer 209, and cover layer 211 may be attached together by way of, for example, suitable adhesive, welding processes, or other attachment methods, so as to render the assembled patient mountable portion 101 impervious to fluids and consistent with a device that can be used in a sterile environment.

In some embodiments, base layer 209, cover layer 211, or an intermediate layer (not shown) integrated in or attached to multifunction device 100 may serve as a shielding layer designed to isolate position indicating elements 203 and 205 from stray electromagnetic signals such as, for example, those that might be generated by the heart or other stray electrical signals.

In some embodiments, memory device 207 may comprise generally a preprogrammed device such as, for example, a read-only memory (ROM) or serial ROM (SROM). In some embodiments, the memory device may not be capable of being erased or re-programmed. In some embodiments memory device may be programmed with some or all of the following information:

1) a serial number;

2) an encrypted key, used to associate the serial number with a valid multifunction device, thus enabling a supplier to securely verify certain information such as, for example, that multifunction device 100 is valid to be used with a corresponding image guided surgery system, that multifunction device 100 is used only one time and not repeatedly reused, or other information;

3) information regarding the location of position indicating elements 203 and 205 With respect to:

a. properties such as impedance, resistance, magnetic moment, or other properties, thereby reducing the tolerances by which position indicating elements 203 and 205 must be manufactured, or b. location and orientation of position indicating elements 203 and 205 with respect to one another and with respect to the origin of coordinate system 111 that is associated with multifunction device 100, thereby reducing the mechanical tolerances required in manufacturing necessary to produce a device that achieves a consistent accuracy;

4) information concerning the location, orientation, and nature of one or more embedded fiducial markings or imageable patterns (both of which are discussed in detail below) that may be present on multifunction device 100 relative to the origin of coordinate system 111 of multifunction device 100, thereby reducing the mechanical tolerances required in manufacturing necessary to produce a device that achieves a consistent accuracy;

5) information concerning the location of the integrated divots 105 relative to the origin of coordinate system 111 of multifunction device 100, thereby reducing the mechanical tolerances required in manufacturing necessary to produce a device that achieves a consistent accuracy;

6) general information regarding model number, manufacture date, expiry date, lot number, or other information regarding multifunction device 100;

7) information regarding pin connections of the different layers of multifunction device 100;

8) information regarding what layers are included in multifunction device 100, their relative position and orientation in relation to position indicating elements 203 and 205;

9) in some embodiments, magnetic moments and other parameters necessary to characterize additional receiving or transmitting elements that may be embedded in multifunction device 100; or other information.

In one embodiment, memory device 207 may be incorporated into a cable or plug associated with multifunction device 100. In other embodiments (as illustrated in FIG. 2), memory device 207 is an integral part of the assembled device that cannot be separated or removed from the assembly without damaging or otherwise rendering the assembly inoperable. In one embodiment, memory device 207 may include a radio frequency identification (RFID) type of device that is capable of wirelessly transmitting the aforementioned information using methods that are known in the art.

FIGS. 3A and 3B illustrate perspective and planar views of circuit board 201 according to an embodiment of the invention. In some embodiments, multifunction device 100 may include fiducial marks 301. Fiducial marks 301 may include marks made of a material that is imageable by an imaging modality (e.g., a radio-opaque material that is visible on an x-ray). Fiducial marks 301 may be embedded within multifunctional device 100 and are shown in FIGS. 3A and 3B attached to circuit board 201. Fiducial marks 301 are shown in FIGS. 3A and 3B as different, distinguishable flat patterns (dash, plus sign, triangle, circle—other shapes may be used). However, three-dimensional shapes such as spheres, cubes, pyramids, cylinders, or other three-dimensional shapes may be used. Fiducial marks 301 are shown in FIGS. 3A and 3B as attached to circuit board 201, but could equally be attached to another part of multifunction device such as, for example, cover layer 211, base layer 209, or other part of multifunction device 100, so long as the relative location of the fiducial marks remains fixed relative to the origin of coordinate system 111 of multifunction device and position indicating elements 203 and 205.

Figure 4A:
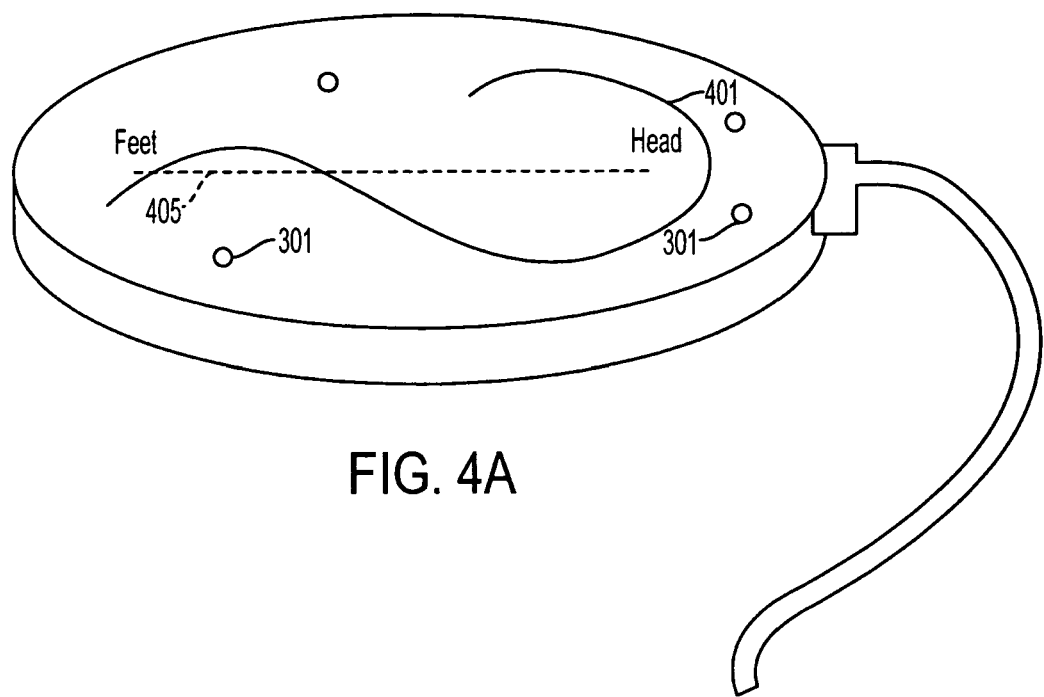
FIG. 4A illustrates a multifunction device according to an embodiment of the invention.
Figure 4B:
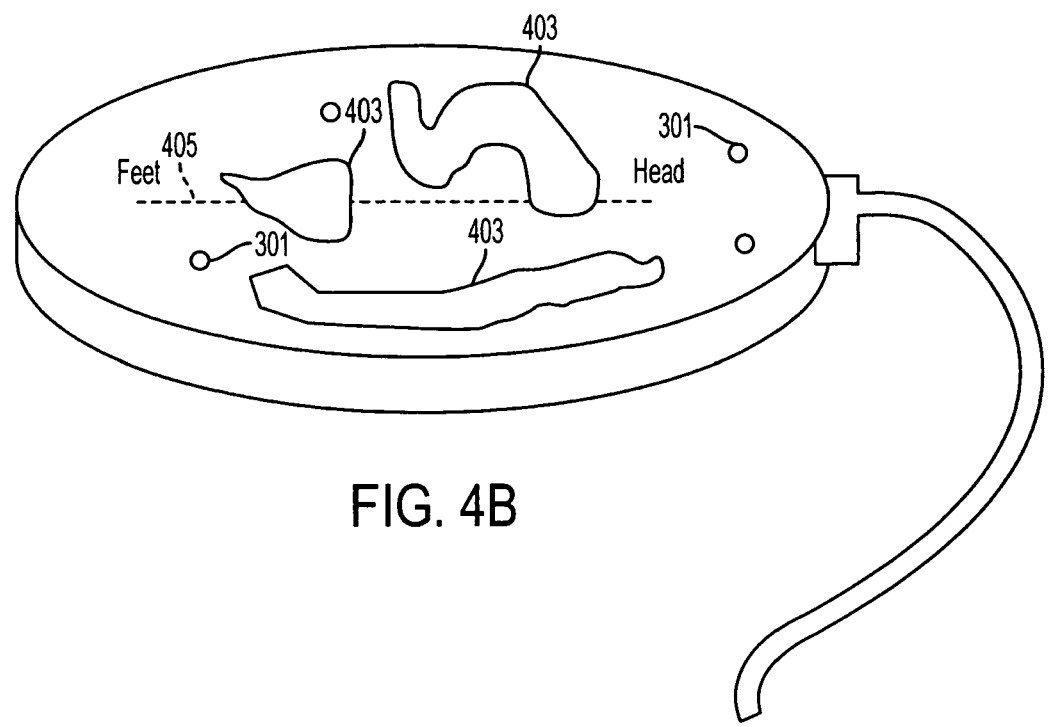
FIG. 4B illustrates a-multifunction device according to an embodiment of the invention.

FIGS. 4A and 4B illustrates multifunction device 100 according to an embodiment of the invention, wherein multifunction device 100 includes one or more "imageable patterns." In some embodiments, the one or more imageable patterns may take the form of imageable pathways 401 or imageable regions 403. Fiducial marks 301, 303 or other fiducial marks may also be used in or as imageable patterns. Imageable pathways 401 may include conduits that are visible to an imaging modality. In some embodiments, imageable pathways 401 and/or imageable regions 403 may be used instead of or in addition to fiducial marks 301. Imageable pathways 402 may be made through the use of an imageable material (e.g., radio-opaque material that is visible to via an x-ray) placed on multifunction device 100. For example, when fluoroscopy is used as an imaging modality, imageable pathway 401 may take the form of a tube or groove in multifunction device 100 that has been filled with a barium compound. In some embodiments, imageable pathways 401 may include three-dimensional paths. In some embodiments, imageable pathways 401 may be multiply curved paths whose geometry is well established at the time of manufacture. These multiply curved paths may define a unique orientation and location of multifunction device 100. Furthermore, complex imageable pathways 401 may provide superior registration to fiducial marks alone because they include a continuum of points rather than the discrete set of points provided by fiducial marks alone. Imageable regions 403 may also be used in a similar fashion and may include zones of unique geometry that are filled with an appropriate material (e.g., one that renders them visible to an imaging modality).

Referring back to FIGS. 3A and 3B, in one embodiment, fiducial marks 301 may be deposited directly onto circuit board 201. In some embodiments, fiducial marks 301 may be deposited near the ends of position indicating elements 203 and 205 as shown in FIGS. 3A and 3B. In some embodiments, fiducial marks 301 may be identifiable uniquely from their geometric shape (e.g., crosses, dashes, triangles, circles, or other shape). Additionally, fiducial marks 301 may be arranged in an asymmetric manner so that they may be readily identified on planar images by comparing the distance between marks and the angles between lines created by joining two marks to a third apex mark.

Additional fiducial marks may also be placed on or within the device. For example, as illustrated in FIGS. 3A and 3B, fiducial marks 303 may exist on circuit board 201 or elsewhere on multifunction device 100. In some embodiments, one or more fiducial marks 301 and/or 303 may be represented out of the plane formed by the generally two-dimensional circuit board 201. In some embodiments, one or more fiducial marks 301 and/or 303 may be represented in a special location relative to divots 105. Furthermore, in some embodiments, divots 105 may enjoy a special relationship with the location of position indicating elements 203 and/or 205, such as, for example, a divot may be located near the origin of coordinate system 111 of multifunction device 100, the location of individual sensor origins 305 and 307 of sensors 203 and 205 respectively, and/or other feature of multifunction device 100.

In some embodiments, fiducial marks 301 and/or 303 may be visible from substantially perpendicular views taken by an imaging modality such as, for example, a fluoroscope, to assist in "fluoroscopic image guided surgery," also known as "fluoronav" image guided surgery. In this technique (cf. Livyatan, *Calibration and Gradient-based Rigid Registration of Fluoroscopic X-rays to CT, for Intra-Operative Navigation*, MSc Thesis School of Computer Science and Engineering, The Hebrew University of Jerusalem, Israel; 2003 (Professor Leo Joskowicz, supervisor)), parameters of a fluoroscope are determined by examining shadows cast by fiducial marks 301 and/or 303 as x-rays pass from the fluoroscope emitter through multifunction device 100 to the fluoroscope image intensifier. This may be done in several fluoroscope positions and orientations. In each fluoroscope position, the location of multifunction device 100 (and therefore any fiducial marks 301/303 contained therein) in image space (e.g., the frame of reference of the fluoroscope) and sensor space (e.g., the frame of reference of a tracking device) is determined to correctly determine the parameters necessary for fluoroscopic image guided surgery.

Figure 5:
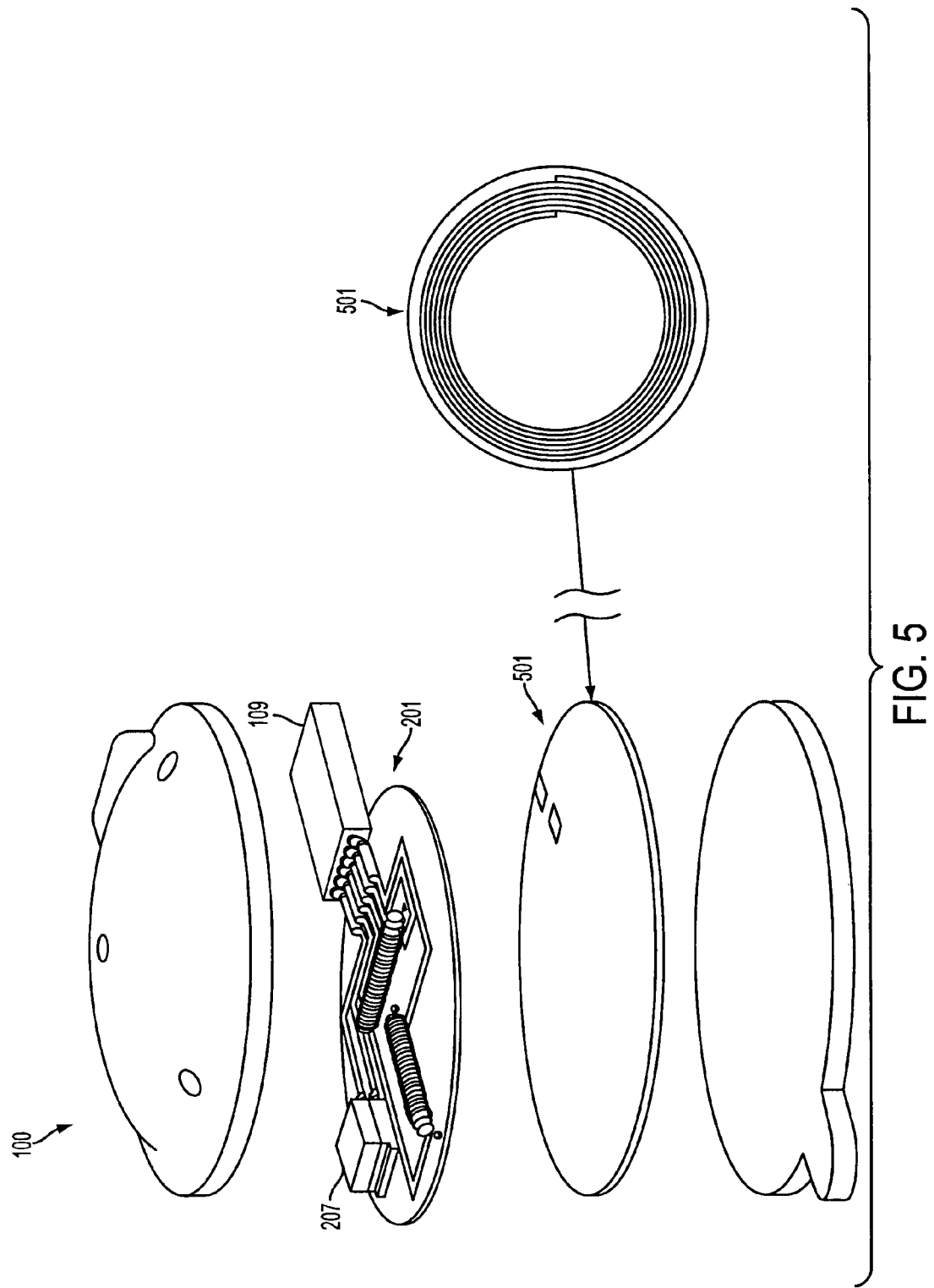
FIG. 5 illustrates a multifunction device according to an embodiment of the invention.

FIG. 5 illustrates multifunction device 100 according to another embodiment of the invention, wherein multifunction device 100 includes a layer that contains an integrated monitor 501 capable of measuring a physiological parameter such as, for example, heart contractions (an electrocardiograph [ECG] electrode), breathing motion, or other physiological parameter.

Integrated monitor 501 may not only be used for gathering data regarding a physiological parameter, but also for gating the acquisition of image data (e.g., computerized tomography data during a CT scan or other data gathered by an imaging modality) or gating the use of multifunction device 100 as a position indicating element in a tracking device. FIG. 5 illustrates a cardiac monitoring electrode as integrated monitor 501. A similar device and appropriate circuit board layer may be incorporated to monitor respiratory motion using technology that is known in the art. In some embodiments, signals or other data gathered by integrated monitor 501 may be fed back through the common connector 109. In one example, wherein integrated monitor 501 comprises an ECG electrode, the layer containing integrated monitor 501 may be composed of carbon fiber and may include an integrated conductive gel containing propylene glycol or similar material. Information regarding the properties of integrated monitor 501 may be programmed into memory device 207. In some embodiments, connectors for integrated monitor 501 may be similar to those commonly used in the art such as, for example, a "snap" connector. In some embodiments, connectors for integrated monitor may be integrated into the same plug utilized by position indicating elements 203 and 205.

Figure 6:
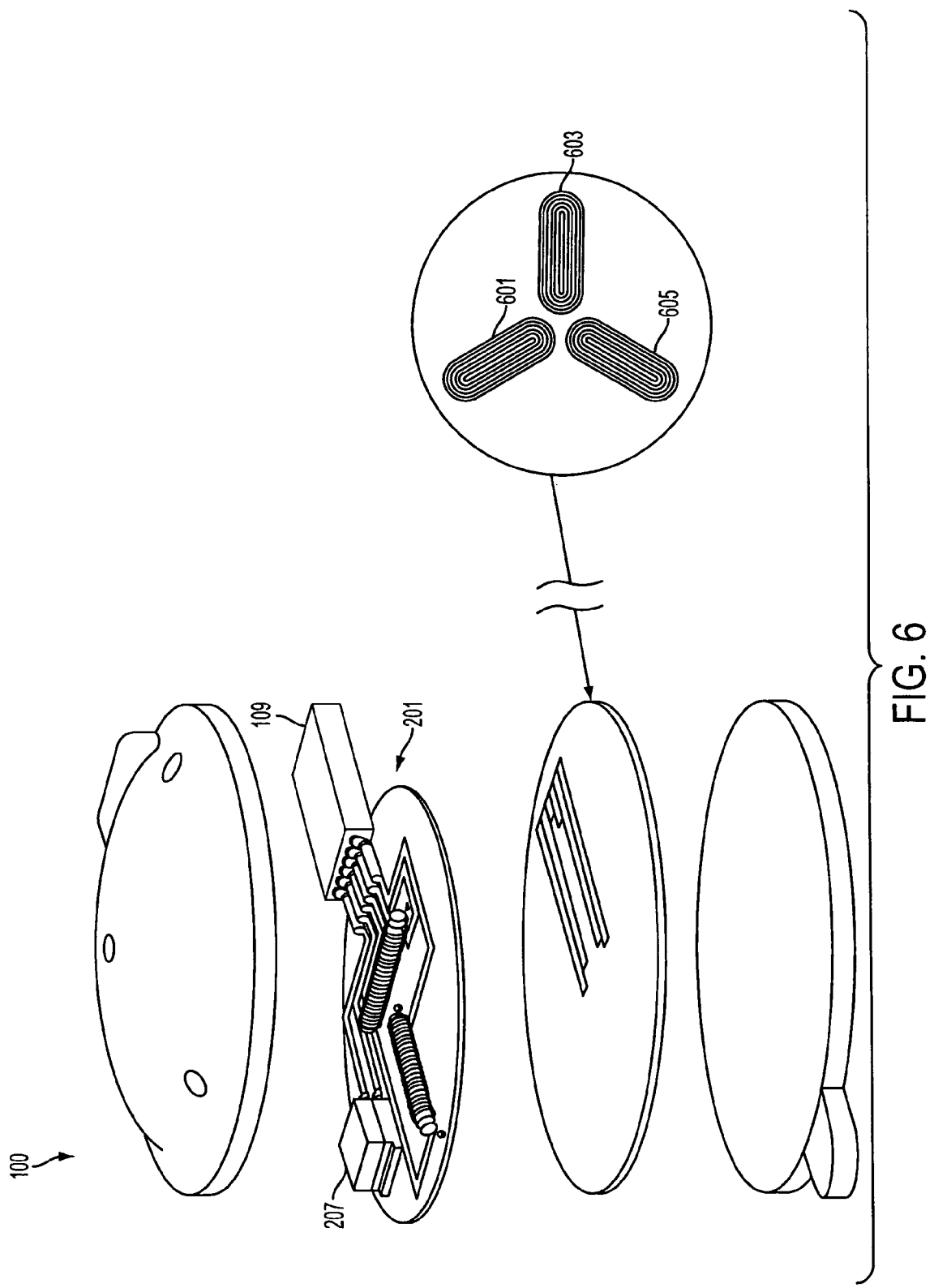
FIG. 6 illustrates a multifunction device according to an embodiment of the invention.

FIG. 6 illustrates multifunction device 100 according to another embodiment of the invention, wherein multifunction device 100 includes a layer that contains antennae 601, 603, and 605. Antennae 601, 603, and 605 may serve numerous purposes such as, for example, energizing a wireless transmitter, receiving signals from a wireless transmitter (such as, for example, an RFID tag or wireless transceiver) that is capable of indicating the position and orientation of a separate position indicating element embedded in the body of a patient (e.g., a "surgical" position indicating element). In one embodiment, numerous individual multifunction devices or a single large multifunction device may take the place of the excitation/receive coils of a field generator of a tracking device. Normally, the excitation or receive coils of such a field generator are housed within a separate unit. In this embodiment, multifunction device 100 acts as a field generator in place of (or in addition to) the separate field generation unit. This embodiment may increase the sensitivity of the tracking device and reduce the space requirements of the field generator. It may also be used as an intrinsic dynamic reference, as a field generator integrated into multifunction device 100 that is placed on the patient will move with the patient.

In some embodiments, additional functional and/or passive layers may be integrated into the basic design of multifunction device 100 described herein by adding additional layers. Thus, providing further features of multifunction device 100 such as, for example:

1) A layer containing a magnetic resonance (MR) imaging coil capable of locally measuring an MR field in the region of multifunction device 100;

2) A layer containing an ultrasound transducer capable of generating and delivering as well as receiving ultrasonic energy for focused ultrasound;

3) A layer containing a three dimensional pattern comprising, for example, ball bearings that can be used to calculate fluoroscope parameters (or other parameters for an imaging modality), wherein the three-dimensional pattern is unique when viewed from multiple orientations.

4) A layer containing a pattern of at least three radiodense regions forming a checkerboard with non radiodense regions (this could also be a complex two dimensional pattern). Such a pattern may be used to accurately track multifunction device 100 fluoroscopically (to assist in tracking patient motion in a second manner).

In some embodiments, multifunctional device 100 may be manufactured using simple techniques and may be calibrated and programmed after it is assembled, obviating the need for high tolerance assembly techniques.

In some embodiments, the surface of multifunction device 100 may be pre-imprinted with a body-centric coordinate system such as, for example, arrows, lines, dashes, or other indicators pointing toward, for example, the head, feet, left, and/or right of the patient. These markings may visible to a surgeon and used by him or her to roughly orient the patch on the patient, enabling software to provide more relevant feedback to the surgeon. Examples of such marks are indicated as items 405 in FIGS. 4A and 4B.

In other embodiments, multifunction device 100 may be composed of a plurality of individual patches containing at least one position indicating element and/or other devices discussed above. When the multiple individual patches are connected to a patient, a calibration step may be performed to determine the exact locations of the position indicating elements so that tracking can occur. This calibration step may be done either using an imaging modality or by moving a field generator associated with the tracking device of the position indicating elements to multiple locations.

In one embodiment multifunction device 100 may be utilized in performing different roles in image guided surgery. For example, divots 105 or other surface features of multifunction device 105 may be used as discrete markings or "landmarks" for a point registration.

Furthermore, position indicating elements 203 and 205, as well as fiducial markings 301 and 303, and coordinate system 111 may be used for other types of registration, dynamic referencing, verification of registration, and/or other purposes. For example, position indicating elements may be used to provide position information regarding one or more points on the surface of a patient's skin in the frame of reference of a tracking device. Fiducial marks 301 and 303 may be used in conjunction with an imaging modality to provide position information in an image space. This position information may then be used in the registration of the corresponding area of the patient's anatomy. Additionally, position indicating elements 203 and 205 may be used to track movement of a patient for use in dynamic referencing during image guided surgery.

In some embodiments, multifunction device 100 may be connected to or used in conjunction with a radio-opaque grid that may be applied to a patient. This enables devices to be guided by the grid/multifunction device 100 combination by imaging the grid and multifunction device 100 simultaneously. Once the system is registered and a target area or point (e.g., an area or point of interest within a patient) is located on associated images of the patient, the closest gridmark may be identified and used to assist in placement of a therapeutic or diagnostic device (e.g., a needle) at the target area or point due to the fact that the grid marks are known relative to multifunction device 100.

Imageable pathways 401 and/or imageable regions 403 may also be used to obtain, via an imaging modality, image space position information regarding a portion of the patient's anatomy for use in registration, verification of registration, or for other purposes. These complex three-dimensional imageable patterns may be readily and unambiguously identified on images. Additionally, they provide a plethora of position information, which assists in performing a high quality registration. Furthermore, the three-dimensional patterns may be visible from a number of different positions/orientations of an imaging modality such as, for example, a fluoroscope or other imaging modality. Imageable pathways 401 and/or imageable regions 403 may also be used in conjunction with fiducial marks 301 and 303 to obtain image space information.

As indicated above, in some embodiments, imageable pathways 401, imageable regions 403, and or fiducial marks 301 and 303 may exist on multifunctional device 100 in a known spatial relationship to position indicating element 203, position indicating element 205, and/or coordinate system 111 of multifunction device 100. For example, the coordinates of fiducial markers 301 and 303 may be known in coordinate system 111. Determination of the location of position indicating elements 203 and 205 in the coordinate system 150 of a tracking device (e.g., the patient space) may be used to determine the location of fiducial marks 301 and 303 in the patient space (because of the known relationship between position indicating elements 203/205 and fiducial marks 301/303). Images that contain fiducial marks 301 and 303 enable their locations to be determined in image space, thus, allowing registration to be performed between the image space and the patient space. In general, this known relationship may aid in registering patient-space position information provided by position indicating elements 203 and 205 and/or coordinate system 111 to image-space information provided by imageable pathways 401, imageable regions 403, and/or fiducial marks 301 and 303.

As mentioned above, integrated monitor 501 may be used to obtain physiological parameters from a patient and/or for gating the sampling of position information or image information used in image guided surgery according to those physiological parameters.

Furthermore, antennae 601, 603, and 605 may be used to provide various features of multifunction device such as, for example, a magnetic field for use with position indicating elements within the patient as part of a tracking device, as part of a CT, MR, ultrasound or other imaging modality, or for other uses.

Figure 7:
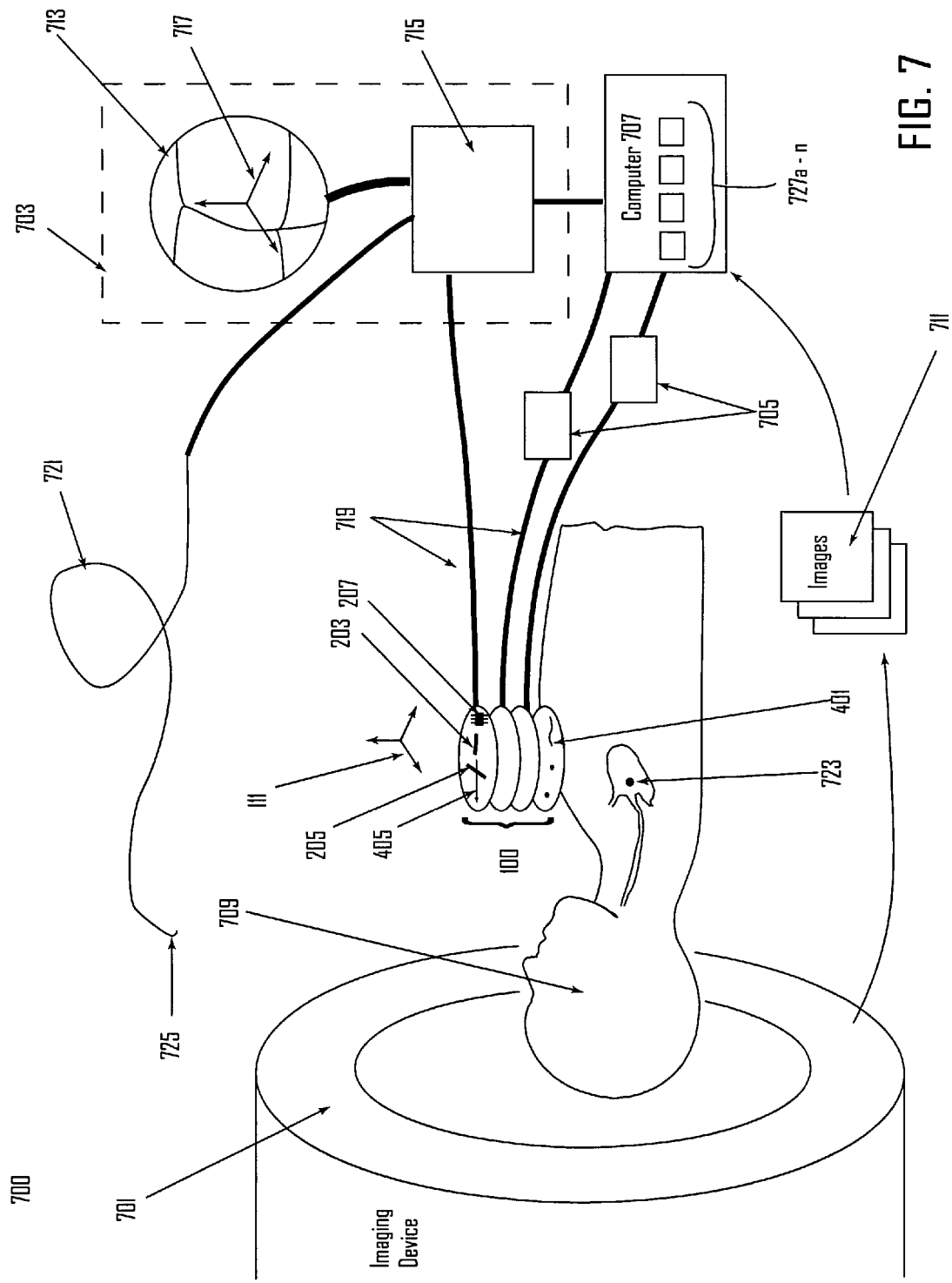
FIG. 7 illustrates a system for performing computer-assisted surgery according to an embodiment of the invention.

FIG. 7 illustrates a computer assisted surgery system 700 according to one embodiment of the invention. In one embodiment, system 700 may include an imaging device 701, a tracking device 703, one or more physiological measuring devices 705, a computer 707, and/or other elements. In some embodiments, physiological measuring devices 705, may be connected to computer 707 directly. In other embodiments, physiological measuring device 705 may be connected through tracking device 703 (not illustrated) which may then relay information to computer 707 or use the information, for example, to gate position data from position indicating elements 203 and/or 205 in multifunction device 100.

In some embodiments, tracking device 703 may comprise a field generator 713 and a control unit 715. In some embodiments, tracking device 703 may comprise, for example, an electromagnetic tracking device. In which case field generator 713 may include a magnetic field generator and any associated position indicating elements 203 and/or 205 may comprise magnetic position sensors. Tracking device 703 may be associated with a coordinate system 717 (similar to or the same as coordinate system 150 of FIG. 1).

During a surgical procedure, other components may be connected to multifunction device 100 such as, for example, wiring elements 719, which may connect multifunction device 100 to tracking device 703 or physiological measuring devices 705. In one embodiment, the layer of the multifunction device containing position indicating elements 203 and 205 (e.g., circuit board 201 of FIG. 2) may be connected to tracking device 703. Position indicating elements 203 and 205 may be sampled by tracking device 703 to provide position and/or orientation information regarding position indicating elements 203 and 205 to computer 707 in the frame of reference of tracking device 703 (e.g., coordinate system 717). In one embodiment, physiological parameters of a patient 709 may be measured by physiological measuring devices 705 and transferred to computer 707.

Figure 8:
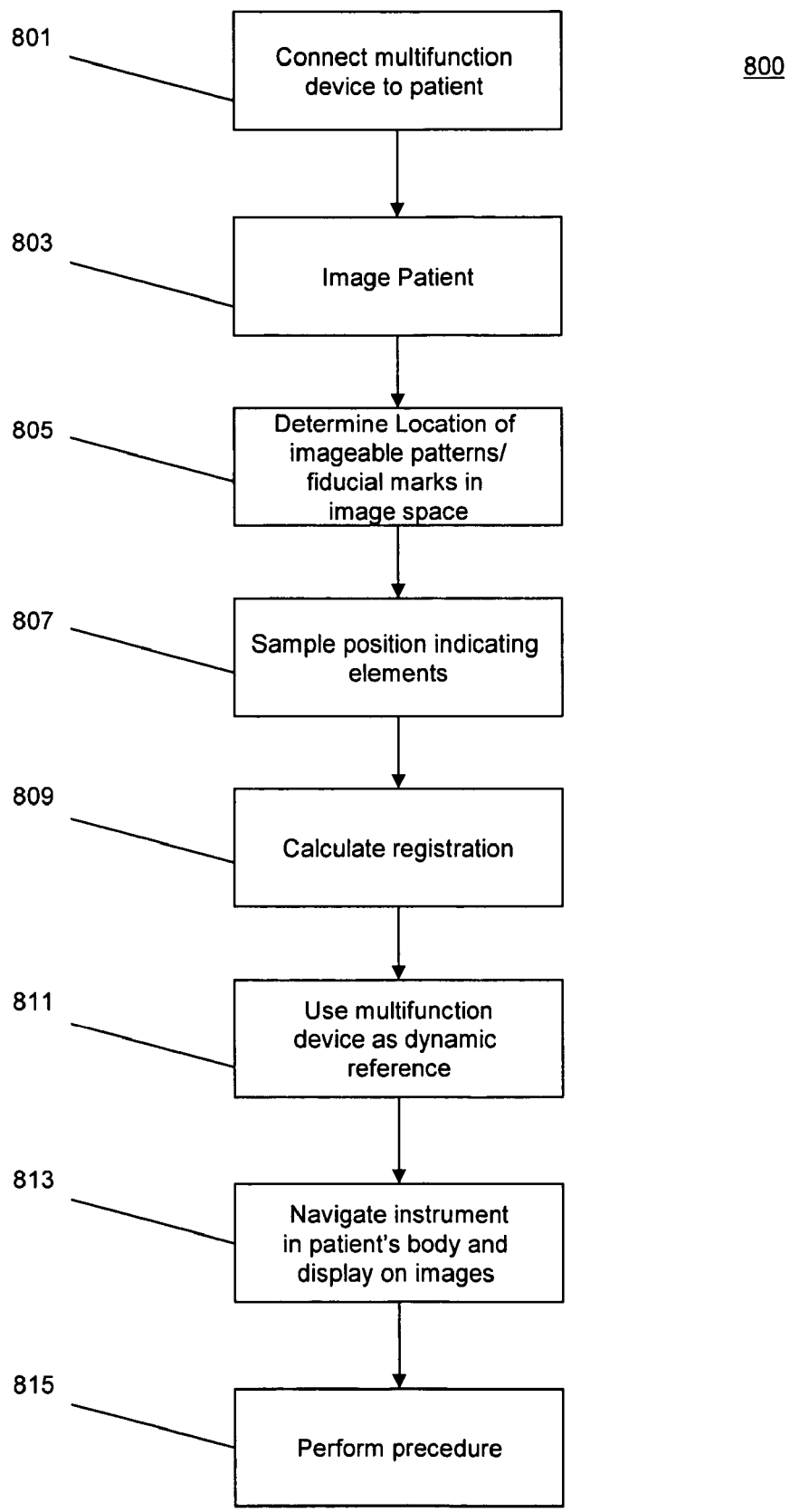
FIG. 8 illustrates a process for imaging a surgical instrument within a patient during a surgical intervention according to an embodiment of the invention.

FIG. 8 illustrates a process 800, wherein multifunction device 100 may be used as part of system 700 for performing image guided surgery. In an operation 801, multifunction device 100 may be connected to a patient 709. In an operation 803, one or more images 711 of patient 709 may be obtained using imaging device 701. Imaging device 701 may include, for example, a computerized tomography (CT) device, a magnetic resonance (MR) device, a positron emission tomography (PET) device, a fluoroscope, an x-ray device, or other imaging modality. Images 711 may then be loaded onto or stored in computer 707. In some embodiments, images 711 may be obtained when patient 709 is in a known physiological state (e.g. peak inspiration). In some embodiments, the physiological state of patient 709 may be measured/monitored during imaging by multifunction device 100.

In an operation 805, the location/geometry of fiducial marks (e.g., fiducial marks 301 and/or 303) or imageable patterns (e.g., imageable pathways 401 and/or imageable regions 403) incorporated into multifunction device 100 may be determined using images 711 in coordinate system 111 of images 711 (e.g., the image space).

In an operation 807, tracking device 702 may sample position indicating elements 203 and/or 205 of multifunction device 100. This may produce position and/or orientation information of position indicating sensors 203 and/or 205 in the coordinate system 717 of tracking device 703 (e.g., the patient space). This position and/or orientation information may then be provided to computer 707.

In an operation 809, a registration between the image space and the patient space may be calculated. This may be accomplished by combining the location of fiducial marks 301/303 and/or imageable patterns of multifunction device 100 in coordinate system 111 of images 711 (image space) with the location of position indicating elements 203/205 in coordinate system 717 of the tracking device 702 (patient space). This is possible because the location of fiducial marks 301/303 or imageable patterns (imageable paths 401 or regions 403) are known relative to position indicating elements 203/205. In an embodiment, these relationships/relative locations may be programmed into and/or stored into memory device 207 that is associated with multifunction device 100. In cases where the position indicating elements 203 and 205 can be detached from the multifunction device 100, reattachment positions must be consistent and known or it will not be possible to determine the location of fiducial marks 301/303 or imageable patterns from the location of position indicating elements 203/205.

In one embodiment, by making use of the physiological information obtained by physiological measuring devices 705, sampling of position indicating elements 203/205 by tracking device 703 can be gated to coincide with repeatable physiological cycles (e.g. heartbeat or respiratory state), thereby increasing the registration accuracy. In an operation 811, after registration has been performed, multifunction device 100 may begin to function as a dynamic reference device in which, together with the physiological measurements provided by physiological measuring devices 705, more accurate referencing can be obtained than could be otherwise obtained using multifunction device 100 alone. This is because each time a particular gating signal is received, the organs in the patient's body are in the same state, and the position of them is not merely compensated for as would be using dynamic referencing alone.

In an operation 813, a medical instrument/device such as a guidewire 721 (or other instrument such as, for example, a catheter) in which at least one position indicating element (e.g., a "surgical" position indicating element) has been attached, may be navigated in the patient's body and the location of guidewire 721 may be displayed on images 711 (or versions or derivations thereof) relative to multifunction device 100. Further accuracy may be obtained if the position of guidewire 721 is gated according to at least one physiological parameter measured by physiological measuring devices 705 (which, in some embodiments, operate in conjunction with sensors 501 of multifunction device 100). Such gating may act to display the position of guidewire 721 on images 711 only when the physiological parameters match those under which images 711 were obtained (e.g. peak inspiration corresponding to breath hold during the scan). In an operation 815, guidewire 721 or other surgical instrument may be navigated in the patient to perform an intervention (e.g., surgical procedure, diagnostic procedure, or other procedure).

Figure 9:
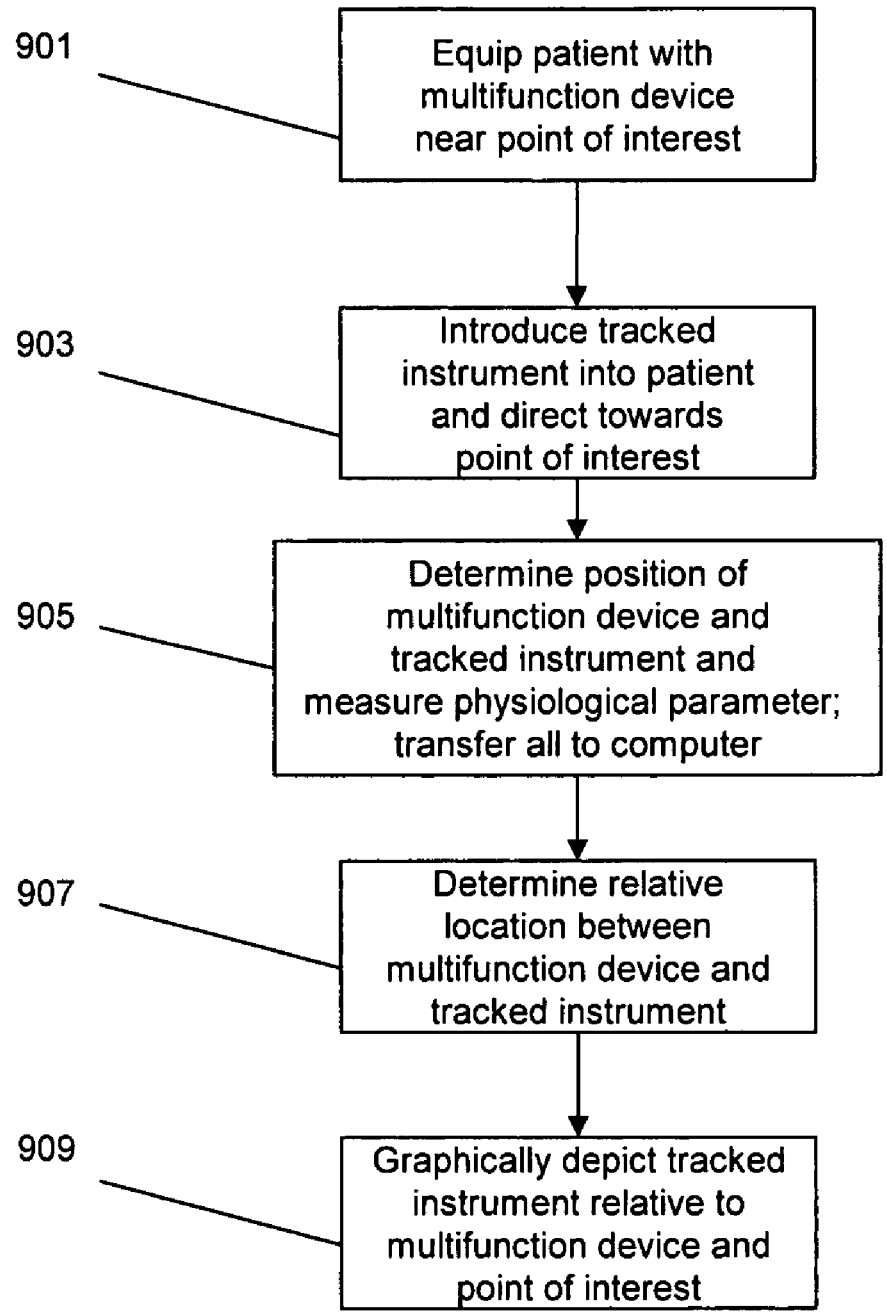
FIG. 9 illustrates a process for utilizing a multifunction device as a proxy-target according to an embodiment of the invention.

FIG. 9 illustrates a process 900 according to an embodiment of the invention, wherein multifunction device 100 may act as a "proxy target" that can be navigated toward in conjunction with an imageless computer assisted surgery system. In an operation 901, patient 709 may first be equipped with multifunction device 100, placed directly over a point of interest 723 (e.g., a "target") such as, for example, the superior vena cava of the heart, with the aim of, for example, placing the exit of a peripherally inserted central catheter (PICC) at point of interest 723. In an operation 903, a medical instrument such as, for example, vascular guidewire 721 (or other instrument such as for example, a catheter), that has been modified to contain a position-indicating element (e.g., a "surgical" position indicating element) near its tip 725, is introduced into the patient (for example into a vein or artery connected to the point of interest 723) and directed toward the point of interest 723. In an operation 905, as guidewire 725 is directed toward point of interest 723, the position of multifunction device 100, the position of guidewire 721, and the physiological parameters measured by physiological measuring devices 705 can be determined and transferred to computer 707. In an operation 907, the relative location between the position of multifunction device 100 and the position of guidewire 723 may then can be calculated. In an operation 909, tip 725 of guidewire 721 may also be graphically depicted relative to the multifunction device 100 (acting as a "proxy target") and therefore graphically depicted relative to point of interest 723. Knowledge of the physiological parameters may increase accuracy as before by enabling sampling only in particular physiological states of the patient (e.g., gating). If multifunction device 100 is oriented such that the body-centric coordinate system markings 405 (see FIGS. 4 and 7) on the multifunction device correspond in an intuitive way to the patient position, the physician performing the intervention will furthermore be able to understand the direction of any deviations of guidewire 721 from the intended direction, which is toward point of interest 723.

In another embodiment utilized for imageless computer assisted surgery, a guidewire 721 (or other instrument such as, for example, a catheter) may be used to determine its proximity to the heart by measuring its motion during different phases of the heart cycle as determined by physiological parameter measurement by multifunction device 100. The closer guidewire 721 is to the heart, the more extreme its motion relative to the multifunction device 100 will be, and the closer the phase of the motion will match that of the heart (as measured by physiological parameter measuring devices 705) compared to the periphery where there may be a time lag before the "beat" of the heart causes guidewire 721 to move. In another embodiment, guidewire 721 may be used to measure the size of a vessel or conduit of patient 709 in which it is located by placing a position indicating element of guidewire 721 near its bent tip 725 and axially spinning the guidewire. Inside small vessels it's rotation will prescribe a line as bent tip 725 will be mostly constrained by the vessel walls. Inside larger vessels where bent tip 725 is allowed to take its natural shape, it will prescribe a circle, the diameter of which is an indication of the vessel size up to a maximum size determined by the amount of bend of bent tip 725.

Imageless computer assisted surgical methods need not involve the heart, but may be used for numerous medical procedures such as, for example assisting in placing a feeding tube into the stomach or small intestine of a patient or for other purposes.

In one embodiment, computer 707 may include one or more software modules 727a-n for performing various features and functions of the invention. In one embodiment, computer 707 may include a module that determines, from images 711, the locations/geometry of the fiducial marks 301, 303, imageable paths 401, imageable regions 403 and or other imageable patterns or elements in the coordinate system of images 711 and/or in the coordinate system of tracking device 713. In another embodiment, computer 707 may include a module that calculates a registration between images 711 (and/or data therefrom) and tracking device 703 (and/or data therefrom). In one embodiment, computer 707 may include a module that calculates and/or depicts the relative location between a position of multifunction device 100 and a position of vascular guidewire 721. Computer 707 may also include a module that graphically depicts guidewire 721 (and/or the tip 725 of guidewire 721) on images 711 relative to multifunction device 100 and therefore to object of interest 723. Computer 707 may also include other modules for performing other features or functions of the invention described herein. In some embodiments, some of these tasks may be performed on or transferred to control unit 715 of tracking device 703.

Those having skill in the art will appreciate that the invention described herein may work with various system configurations. It should also be understood that various software modules 727a-n that are utilized to accomplish the functionalities described herein may be maintained on computer 707, control unit 715, or other components of the invention, as necessary. In other embodiments, as would be appreciated, the functionalities described herein may be implemented in various combinations of hardware and/or firmware, in addition to, or instead of, software.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

I claim:

1. An integrated skin-mountable multifunction device for use with an image guided surgical system, the device comprising:
   a plurality of layers, each layer performing one or more specific functions, including:
   a first layer that includes a patient mountable surface;
   a second layer that includes at least one position indicating element;
   at least one imageable pattern whose geometry is known in a coordinate system of the at least one position indicating element, wherein the imageable pattern is visible on an imaging modality; and
   a cover layer, wherein each of the plurality of layers are removable from one another and wherein the device is configured to accept one or more additional layers for performing additional functions between the first layer and the cover layer, wherein the second layer comprises a circuit board having the at least one position indicating element mounted thereon and wherein the imageable pattern is etched on the circuit board.

2. The device of claim 1, wherein the imageable pattern comprises:
   one or more integrated imageable pathways that are uniquely identifiable from images of the device.

3. The device of claim 2 wherein the one or more imagable pathways comprise one or more tubes or grooves within one or more of the plurality of layers of the device.

4. The device of claim 3, wherein the one or more imageable pathways comprise one or more tubes filled with a substance visible to the imaging modality.

5. The device of claim 2 wherein at least one of the one or more imagable pathways comprise a path having multiple curves.

6. The device of claim 2, wherein at least one of the one or more imagable pathways includes a pathway that advances along a three dimensional path.

7. The device of claim 2 wherein the one or more imagable pathways are made visible to the imaging modality by the addition of a radio-opaque material to the one or more imagable pathways.

8. The device of claim 1, wherein the imageable pattern comprises one or more fiducial markers forming a pattern that is uniquely identifiable from images of the device.

9. The device of claim 1, wherein the at least one position indicating element exists in a known relation to a coordinate system associated with the imageable pattern.

10. The device of claim 1, wherein the one or more additional layers include a layer having a monitoring device capable of measuring a physiological parameter of a patient.

11. The device of claim 10, wherein the physiological parameter is one of a heartbeat, heart electrical signals, or a cycle of respiration.

12. The device of claim 1, wherein the one or more additional layers include a layer having an integrated memory device that is programmed with information enabling the device to be uniquely identified.

13. The device of claim 1, wherein the cover layer includes one or more visible markings that indicate a correct placement of the multifunction device on the patient.

14. The device of claim 1, wherein the cover layer further comprises grooves or divots, such that coordinates corresponding to the grooves or divots are obtainable using a tracked probe associated with a tracking device.

15. The device of claim 1 wherein one of the plurality of layers includes a shielding material that isolates the at least one position indicating element from stray electromagnetic signals.

16. The device of claim 1, wherein the one or more additional layers include a layer having one or more antennae thereupon that receive signals from at least a second position indicating element associated with a patient procedure.

17. The device of claim 1, wherein the one or more additional layers include a layer having one or more excitation or receive coils of a tracking device that determines one or more of position or orientation information regarding the at least one position indicating element.

18. The device of claim 1, wherein the one or more additional layers include a layer having at least one ultrasound transducer that generates and receives ultrasonic energy.

19. An integrated skin-mountable multifunction device for use with an image guided surgical system, the device comprising:
   a patient mountable portion comprising a base layer and a cover layer, wherein the base layer is removably attachable to a skin surface of a patient;
   a circuit board located between the base layer and the cover layer having at least one position indicating element attached thereto, the circuit board further including an imageable pattern etched on the circuit board; and
   at least one imageable continuous pathway integrated into the patient mountable portion whose geometry is known in a coordinate system of the at least one position indicating element, wherein the at least one imageable continuous pathway comprises a multiply curved tube or groove that includes a material that is visible to an imaging modality.

20. A method for imaging a surgical instrument within a patient during a surgical intervention performed on the patient using a multifunction device, wherein the surgical instrument is equipped with one or more surgical position indicating elements; wherein the multifunction device includes one or more imageable paths integrated into the multifunction device and one or more external position indicating elements, wherein the one or more imageable paths comprise a multiply curved tube or groove that is visible via an imaging modality, wherein the multifunctional device further includes a circuit board having at least one position indicating element mounted thereon and wherein an imageable pattern is etched on the circuit board, and wherein the position and orientation of the surgical and external position indicating elements may be obtained using a tracking device, the method comprising:
   placing the multifunction device onto the patient;
   obtaining one or more images of the patient, wherein the one or more imageable paths and the imageable pattern are visible on the one or more images;
   receiving image-space data regarding the geometry of the one or more imageable paths and the imageable pattern in the coordinate system of the one or more images;
   receiving patient-space data regarding position information of the one or more external position indicating elements in the coordinate system of the tracking device;
   registering the patient-space data in the coordinate system of the tracking device to the image-space data in the coordinate system of the images; and
   measuring at least one physiological parameter of the patient using the multifunction device,
   displaying the location of the one or more surgical position indicating elements on the one or more images relative to the location of the one or more external position indicating elements, wherein the display is gated by the at least one physiological parameter.

21. The method of claim 20 wherein the at least one physiological parameter includes one or more of respiration activity or heart activity.

22. An integrated skin-mountable multifunction device for use with an image guided surgical system, the device comprising:
- a plurality of layers, each layer performing one or more specific functions, including:
  - a first layer that includes a patient mountable surface;
  - a second layer that includes at least one position indicating element;
  - at least one imageable pattern whose geometry is known in a coordinate system of the at least one position indicating element, wherein the imageable pattern is visible on an imaging modality; and
- a cover layer, wherein each of the plurality of layers are removable from one another and wherein the device is configured to accept one or more additional layers for performing additional functions between the first layer and the cover layer, wherein the one or more additional layers include a layer having at least one magnetic resonance (MR) imaging coil thereupon that measures an MR field in a region of the device.

23. An integrated skin-mountable multifunction device for use with an image guided surgical system, the device comprising:
- a plurality of layers, each layer performing one or more specific functions, including:
  - a first layer that includes a patient mountable surface;
  - a second layer that includes at least one position indicating element;
  - at least one imageable pattern whose geometry is known in a coordinate system of the at least one position indicating element, wherein the imageable pattern is visible on an imaging modality; and
- a cover layer, wherein each of the plurality of layers are removable from one another and wherein the device is configured to accept one or more additional layers for performing additional functions between the first layer and the cover layer, wherein the one or more additional layers include a layer having a pattern of at least three radiodense regions forming a checkerboard with non-radiodense regions.

* * * * *